United States Patent
Choi et al.

(10) Patent No.: US 11,903,685 B2
(45) Date of Patent: Feb. 20, 2024

(54) APPARATUS AND METHOD FOR ESTIMATING BIO-INFORMATION

(71) Applicants: SAMSUNG ELECTRONICS CO., LTD., Suwon-si (KR); Industry-University Cooperation Foundation Hanyang University, Seoul (KR)

(72) Inventors: Jin Woo Choi, Suwon-si (KR); Joon-Hyuk Jang, Seoul (KR); Youn Ho Kim, Hwaseong-si (KR); Chang Mok Choi, Suwon-si (KR); Tae-Jun Park, Seoul (KR); Kwangsub Song, Seoul (KR)

(73) Assignees: SAMSUNG ELECTRONICS CO., LTD., Suwon-si (KR); Industry-University Cooperation Foundation Hanyang University, Seoul (KR)

(*) Notice: Subject to any disclaimer, the term of this patent is extended or adjusted under 35 U.S.C. 154(b) by 643 days.

(21) Appl. No.: 16/817,021

(22) Filed: Mar. 12, 2020

(65) Prior Publication Data
US 2021/0030278 A1 Feb. 4, 2021

(30) Foreign Application Priority Data
Jul. 30, 2019 (KR) .................. 10-2019-0092188

(51) Int. Cl.
*A61B 5/022* (2006.01)
*A61B 5/021* (2006.01)
*A61B 5/00* (2006.01)

(52) U.S. Cl.
CPC .......... *A61B 5/022* (2013.01); *A61B 5/02116* (2013.01); *A61B 5/681* (2013.01);
(Continued)

(58) Field of Classification Search
CPC ... A61B 5/022; A61B 5/02116; A61B 5/6803; A61B 5/681; A61B 5/6843; A61B 5/6879; A61B 5/7267
(Continued)

(56) References Cited

U.S. PATENT DOCUMENTS

| 2013/0218038 A1 | 8/2013 | Zhang |
| 2015/0031965 A1 | 1/2015 | Visvanathan et al. |

(Continued)

FOREIGN PATENT DOCUMENTS

| JP | 2018-067303 A | 4/2018 |
| KR | 10-2017-0048970 A | 5/2017 |

(Continued)

*Primary Examiner* — Alex M Valvis
*Assistant Examiner* — Chanel J Jhin
(74) *Attorney, Agent, or Firm* — Sughrue Mion, PLLC

(57) ABSTRACT

An apparatus for estimating bio-information includes a sensor part configured to measure a pulse wave signal and a contact force of an object, while the object is in contact with the sensor part. The apparatus further includes a processor configured to extract a first feature from the measured pulse wave signal and the measured contact force, select one estimation model from a plurality of estimation models, based on a second feature of a user corresponding to the object, and estimate the bio-information, by inputting the extracted first features in the selected estimation model.

7 Claims, 9 Drawing Sheets

(52) U.S. Cl.
CPC .......... *A61B 5/6803* (2013.01); *A61B 5/6843* (2013.01); *A61B 5/6879* (2013.01); *A61B 5/7267* (2013.01)

(58) Field of Classification Search
USPC ........................................................ 600/301
See application file for complete search history.

(56) References Cited

U.S. PATENT DOCUMENTS

| | | |
|---|---|---|
| 2015/0305632 A1 | 10/2015 | Najarian et al. |
| 2017/0112395 A1 | 4/2017 | Kim et al. |
| 2017/0258340 A1 | 9/2017 | Przybyszewski et al. |
| 2018/0107798 A1 | 4/2018 | Hu |
| 2018/0177413 A1* | 6/2018 | Kwon ................... A61B 5/7445 |
| 2018/0199870 A1* | 7/2018 | Lee .................... A61B 5/14551 |
| 2018/0265095 A1 | 9/2018 | Joe et al. |
| 2019/0008399 A1 | 1/2019 | Mukkamala et al. |
| 2019/0076031 A1 | 3/2019 | Valys et al. |
| 2019/0172587 A1 | 6/2019 | Park et al. |

FOREIGN PATENT DOCUMENTS

| | | |
|---|---|---|
| KR | 10-2018-0079208 A | 7/2018 |
| KR | 10-2019-0011026 A | 2/2019 |

* cited by examiner

APPARATUS AND METHOD FOR ESTIMATING BIO-INFORMATION

CROSS-REFERENCE TO RELATED APPLICATION

This application claims priority from Korean Patent Application No. 10-2019-0092188, filed on Jul. 30, 2019, in the Korean Intellectual Property Office, the entire disclosure of which is incorporated herein by reference for all purposes.

BACKGROUND

1. Field

The disclosure relates to an apparatus and a method for estimating bio-information, and more particularly to technology for cufflessly estimating blood pressure.

2. Description of Related Art

Generally, methods of non-invasively measuring blood pressure without damaging a human body include a method to measure blood pressure by measuring a cuff-based pressure and a method to estimate blood pressure by measuring pulse waves without the use of a cuff.

A Korotkoff-sound method is one of cuff-based blood pressure measurement methods, in which a pressure in a cuff wound around an upper arm is increased and blood pressure is measured by listening to the sound generated in the blood vessel through a stethoscope while decreasing the pressure. Another cuff-based blood pressure measurement method is an oscillometric method using an automated machine, in which a cuff is wound around an upper arm, a pressure in the cuff is increased, a pressure in the cuff is continuously measured while the cuff pressure is gradually decreased, and blood pressure is measured based on a point where a change in a pressure signal is large.

Cuffless blood pressure measurement methods generally include a method of estimating blood pressure by calculating a Pulse Transit Time (PTT), and a Pulse Wave Analysis (PWA) method of estimating blood pressure by analyzing a pulse wave shape.

SUMMARY

According to an aspect of an example embodiment, an apparatus for estimating bio-information includes a sensor part configured to measure a pulse wave signal and a contact force of an object, while the object is in contact with the sensor part. The apparatus further includes a processor configured to extract a first feature from the measured pulse wave signal and the measured contact force, select one estimation model from a plurality of estimation models, based on a second feature of a user corresponding to the object, and estimate the bio-information, by inputting the extracted first features in the selected estimation model.

The sensor part may include a pulse wave sensor including a light source configured to emit light onto the object, and a detector configured to detect light that is reflected or scattered from the object. The sensor part may further include a force sensor configured to measure the contact force when the object comes into contact with the pulse wave sensor and applies pressure to the pulse wave sensor.

The plurality of estimation models may be obtained by classifying a plurality of training data into groups, based on the second feature, and by training a plurality of deep neural networks (DNNs), respectively using the groups into which the plurality of training data is classified.

A first estimation model of a first group corresponding to the second feature that is greater than or equal to a predetermined threshold, may be obtained by training a first deep neural network (DNN), using the first group, and a second estimation model of a second group corresponding to the second feature that is less than the predetermined threshold, may be obtained by training a second DNN different from the first DNN, using the second group.

A first input of the first DNN may include the first feature of the first group, and a second input of the second DNN may include the first feature and the second feature of the second group.

The second feature may include any one or any combination of an initial contact area of the sensor part with which the object is in contact, a last contact area of the sensor part with which the object is in contact, an initial DC component value of the measured pulse wave signal, a last DC component value of the measured pulse wave signal, reference bio-information, a stature of the user, a weight of the user, an age of the user, a sex of the user, ambient humidity, and ambient temperature.

The sensor part may be further configured to measure a contact area of the sensor part with which the object is in contact, while the object is in contact with the sensor part and applies pressure to the sensor part.

The processor may be further configured to obtain a contact pressure, based on the measured contact force and the measured contact area, obtain an oscillometric envelope representing an amplitude of the measured pulse wave signal versus the obtained contact pressure, and extract the first feature from the obtained oscillometric envelope.

The bio-information may include any one or any combination of a blood pressure, a vascular age, an arterial stiffness, an aortic pressure waveform, a vascular compliance, a stress index, and a degree of fatigue of the user.

According to an aspect of an example embodiment, a method of estimating bio-information includes measuring, by a sensor part, a pulse wave signal and a contact force of an object, while the object is in contact with the sensor part, and extracting a first feature from the measured pulse wave signal and the measured contact force. The method further includes selecting one estimation model from a plurality of estimation models, based on a second feature of a user corresponding to the object, and estimating the bio-information, by inputting the extracted first features in the selected estimation model.

The plurality of estimation models may be obtained by classifying a plurality of training data into groups, based on the second feature, and by training a plurality of deep neural networks (DNNs), respectively using the groups into which the plurality of training data is classified.

A first estimation model of a first group corresponding to the second feature that is greater than or equal to a predetermined threshold, may be obtained by training a first deep neural network (DNN), using the first group, and a second estimation model of a second group corresponding to the second feature that is less than the predetermined threshold, may be obtained by training a second DNN different from the first DNN, using the second group.

A first input of the first DNN may include the first feature of the first group, and a second input of the second DNN may include the first feature and the second feature of the second group.

The method may further include measuring a contact area of the sensor part with which the object is in contact, while the object is in contact with the sensor part and applies pressure to the sensor part.

The extracting of the first feature may include obtaining contact pressure, based on the measured contact force and the measured contact area, obtaining an oscillometric envelope representing an amplitude of the measured pulse wave signal versus the obtained contact pressure, and extracting the first feature from the obtained oscillometric envelope.

Additional aspects will be set forth in part in the description that follows and, in part, will be apparent from the description, or may be learned by practice of the presented embodiments.

BRIEF DESCRIPTION OF THE DRAWINGS

The above and/or other aspects, features, and advantages of example embodiments of the disclosure will be more apparent from the following description taken in conjunction with the accompanying drawings, in which.

DETAILED DESCRIPTION

Figure 1:
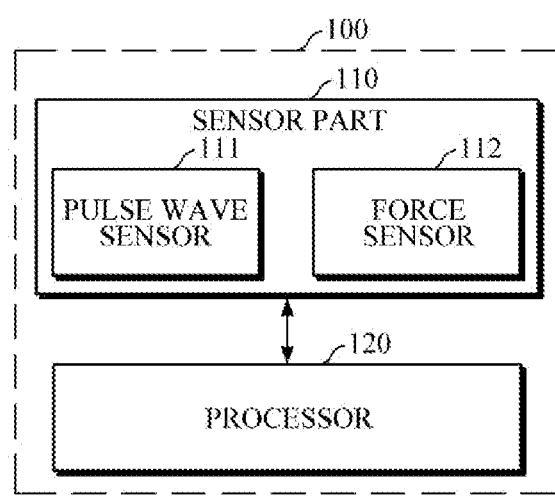
FIG. 1 is a block diagram illustrating an apparatus for estimating bio-information, according to an example embodiment.

Details of example embodiments are included in the following detailed description and drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements may not be limited by these terms. These terms are only used to distinguish one element from another. Also, the singular forms are intended to include the plural forms as well, unless the context clearly indicates otherwise. In the specification, unless explicitly described to the contrary, the word "comprise" and variations, such as "comprise" or "comprising," will be understood to imply the inclusion of stated elements but not the exclusion of any other elements. Terms, such as 'part' and 'module' denote units that process at least one function or operation and they may be implemented by using hardware, software, or a combination thereof.

Hereinafter, example embodiments of an apparatus and method for estimating bio-information will be described in detail with reference to the accompanying drawings.

FIG. 1 is a block diagram illustrating an apparatus 100 for estimating bio-information, according to an example embodiment.

The apparatus 100 for estimating bio-information may be embedded in a medical device used in a specialized medical institution, a smartwatch worn on the wrist, various types of wearable devices such as a smart band type wearable device, a headphone type wearable device, a headband type wearable device, and the like, or a mobile device such as a smartphone, a tablet PC, and the like, but are not limited thereto.

Referring to FIG. 1, the apparatus 100 for estimating bio-information includes a sensor part 110 and a processor 120.

The sensor part 110 may include a pulse wave sensor 111 and a force sensor 112. When a user gradually increases or decreases a pressing force while touching the pulse wave sensor 111 with an object, the pulse wave sensor 111 may measure a pulse wave signal, including a photoplethysmography (PPG) signal, from the object. In this case, the force sensor 112 may measure a contact force between the object and the pulse wave sensor 111.

The pulse wave sensor 111 may include a light source that emits light onto the object; and a detector that detects scattered or reflected light when light emitted by the light source is scattered or reflected from body tissue of the object such as a skin surface or blood vessels.

The light source may include a light emitting diode (LED), a laser diode (LD), a phosphor, and the like, but is not limited thereto. The detector may include one or more pixels, each of which may include a photo diode, a photo transistor (PTO, an image sensor (e.g., CMOS image sensor); and the like. The pulse wave sensor may be formed of an array of a plurality of light sources and/or an array of a plurality of detectors to measure two or more pulse wave signals. In this case, the plurality of light sources may emit light of the same wavelength or light of different wavelengths. The plurality of detectors may be positioned at different distances from the light sources.

The processor 120 may process various operations for estimating bio-information. For example, the processor 120 may control the sensor part 110 upon receiving a request for estimating bio-information from a user or if predetermined criteria for estimating bio-information are satisfied. The processor 120 may be electrically connected to the sensor part 110, and may receive the pulse wave signal and information on the contact force from the sensor part 110.

The processor 120 may provide guide information for guiding a user to measure a pulse wave signal. In this case, the guide information may include information on a contact position or a contact force of an object during a predetermined period of time while a pulse wave signal is measured. For example, to induce a change in amplitude of the pulse wave signal, the information on the contact force may include information for inducing a gradual increase in contact force while an object is in contact with the pulse wave sensor 111; or by contrast, the information on the contact force may include information for inducing a gradual decrease in contact force when a contact force greater than or equal to a predetermined threshold value is applied. In addition, the guide information may include information for guiding a user to adjust a contact force based on actually measured contact force information when the object changes a contact force while being in contact with the sensor part 110.

Further, the processor 120 may estimate bio-information based on the pulse wave signal and information on the contact force. The processor 120 may extract features based on the pulse wave signal and the contact force, and by using the extracted features, the processor 120 may estimate bio-information such as heart rate, blood pressure, vascular age, arterial stiffness, aortic pressure waveform, vascular compliance, stress index, degree of fatigue, skin elasticity, skin age, and the like, but the bio-information is not limited thereto.

For example, the processor 120 may obtain contact pressure, applied by the object to the pulse wave sensor 111, based on the contact force. Further, the processor 120 may obtain an oscillometric envelope that represents an amplitude of the pulse wave signal versus the contact pressure, and may extract features based on the obtained oscillometric envelope.

In addition, the processor 120 may obtain a contact area when the object is in contact with the pulse wave sensor 111 and applies force thereto, and may obtain contact pressure by using the contact force and the contact area. In this case, the sensor part 110 may further include a contact area sensor for measuring a contact area when the object is in contact with the pulse wave sensor 111.

Alternatively, the processor 120 may obtain contact pressure from the contact force by applying a conversion function that defines a correlation between the contact force and the contact pressure. For example, when a user touches the pulse wave sensor 111 with a finger and gradually increases pressure by pressing the sensor with an increasing force, a contact area gradually increases. It can be seen that there is a constant correlation between the contact force, the contact area, and the contact pressure. Accordingly, a conversion function, which converts contact force into contact pressure, may be pre-defined by preprocessing, and the contact force, measured by the force sensor 112, may be converted into contact pressure by using the conversion function. In this case, the conversion function may be defined as various linear or non-linear functions.

Upon extracting the features based on the pulse wave signal and the contact force, the processor 120 may estimate bio-information by using a pre-defied bio-information estimation model. In this case, a plurality of bio-information estimation models may be defined by considering various additional features such as individual characteristics, environment, noise, and the like, and the processor 120 may select an appropriate estimation model based on a user's additional features, and may estimate bio-information by using the selected estimation model.

Figure 2:
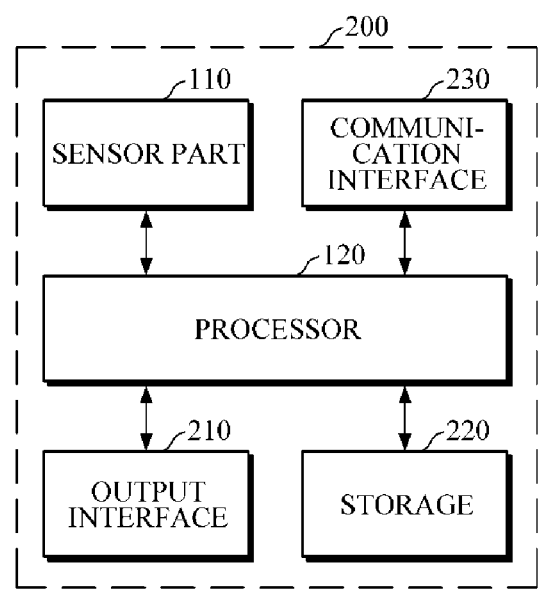
FIG. 2 is a block diagram illustrating an apparatus for estimating bio-information according to, according to an example embodiment.

FIG. 2 is a block diagram illustrating an apparatus 200 for estimating bio-information, according to an example embodiment.

Referring to FIG. 2, the apparatus 200 for estimating bio-information may include the sensor part 110, the processor 120, an output interface 210, a storage 220, and a communication interface 230. The sensor part 110 and the processor 120 are described above with reference to FIG. 1.

The output interface 210 may output processing results of the sensor part 110 and the processor 120. For example, the output interface 210 may visually output an estimated bio-information value and/or guide information through a display, or may non-visually output the information by voice, vibrations, tactile sensation, and the like using a speaker, a haptic module, and the like. A display area may be divided into two or more areas, in which the output interface 210 may output a pulse wave signal, a contact force, and the like, which are used for estimating bio-information, in the form of various graphs in a first area; and along with the information, the output interface 210 may output an estimated bio-information value in a second area. In this case, if the estimated bio-information value falls outside a normal range, the output interface 210 may output warning information in various manners, such as highlighting an abnormal value in red and the like, displaying the abnormal value along with a normal range, outputting a voice warning message, adjusting a vibration intensity, and the like.

The storage 220 may store the processing results of the sensor part 110 and the processor 120. Further, the storage 220 may store a variety of reference information for estimating bio-information. For example, the reference information may include user characteristic information such as a user's age, sex, health condition, and the like. In addition, the reference information may include a variety of information such as a bio-information estimation model, criteria for estimating bio-information, guide information, reference bio-information, and the like, but is not limited thereto.

In this case, the storage 220 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EE-PROM), a Programmable Read Only Memory (PROM), a magnetic memory, a magnetic disk, and an optical disk, and the like, but is not limited thereto.

The communication interface 230 may communicate with an external device by using wired or wireless communication techniques under the control of the processor 120, and may transmit and receive various data to and from the external device. For example, the communication interface 230 may transmit a bio-information estimation result to the external device, and may receive, from the external device, a variety of reference information for estimating bio-information. In this case, the external device may include a cuff-type blood pressure measuring device and an information processing device such as a smartphone, a tablet PC, a desktop computer, a laptop computer, and the like.

In this case, examples of the communication techniques may include. Bluetooth communication, Bluetooth LOW Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, these are examples and are not intended to be limiting.

Figure 3:
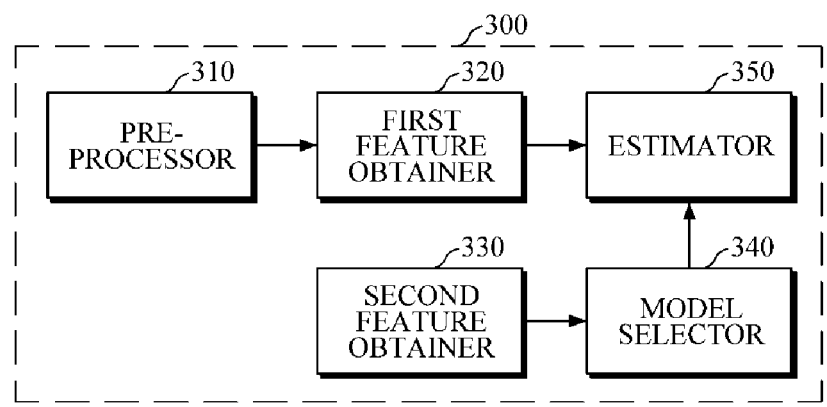
FIG. 3 is a block diagram illustrating a processor of an apparatus for estimating bio-information, according to an example embodiment.
Figure 4A:
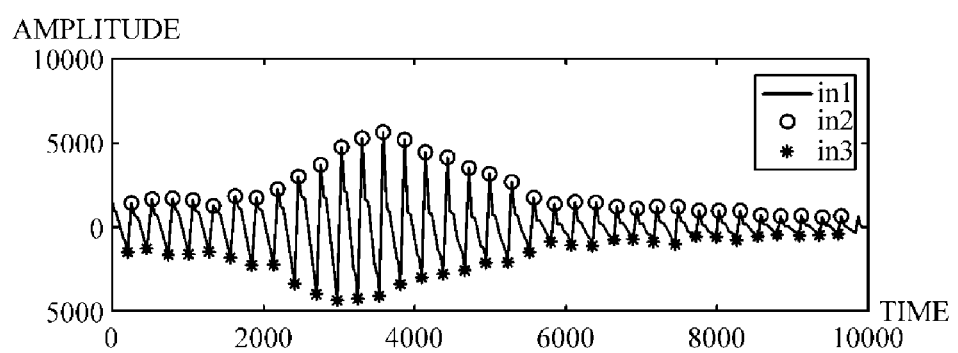
FIGS. 4A and 4B are graphs for explaining an example of obtaining features from a pulse wave signal, according to an example embodiment.
Figure 4B:
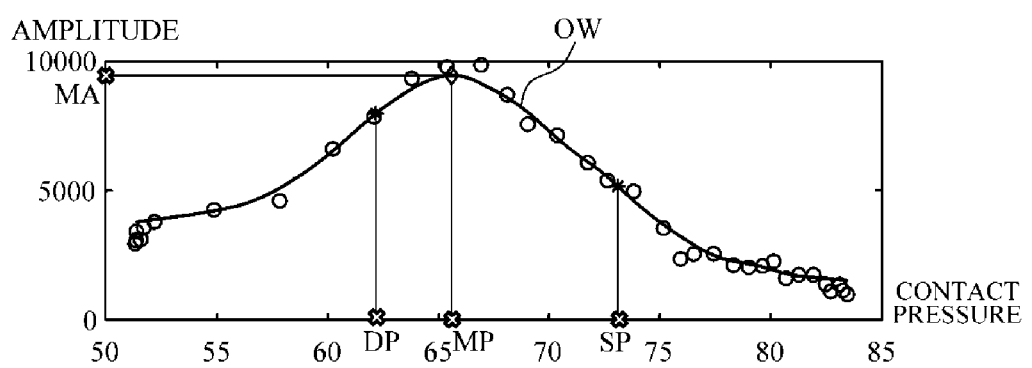

FIG. 3 is a block diagram illustrating a processor 300 of an apparatus for estimating bio-information, according to embodiments. FIGS. 4A and 4B are graphs for explaining an example of obtaining features from a pulse wave signal, according to embodiments.

Referring to FIG. 3, the processor 300 includes a preprocessor 310, a first feature obtainer 320, a second feature obtainer 330, a model selector 340, and an estimator 350.

The preprocessor 310 may receive a pulse wave signal from the pulse wave sensor 111, and may perform preprocessing, including removing noise from the received pulse wave signal. For example, the preprocessor 310 may perform signal correction, such as band-pass filtering, smoothing, ensemble averaging of continuously measured signals, and the like. Further, the preprocessor 310 may detect an outlier based on an amplitude value of the pulse wave signal, a contact force, and the like, and may remove the outlier from the pulse wave signal.

The first feature obtainer 320 may extract a first feature for estimating bio-information based on the received pulse wave signal and the contact force. The first feature obtainer 320 may obtain an oscillometric envelope based on the contact force applied by the object to the pulse wave sensor 111, and may extract a first feature from the obtained oscillometric envelope. As described above, the first feature obtainer 320 may obtain contact pressure between the object and the pulse wave sensor 111 based on the contact force, and may obtain the oscillometric envelope, which represents an amplitude of the pulse wave signal versus the contact pressure, by extracting a peak-to-peak point of the pulse wave signal waveform at each measurement time and plotting the peak-to-peak amplitude at each measurement time against, the contact pressure value at the same point in time.

For example, FIG. 4A illustrates a pulse wave signal measured by the pulse wave sensor 111 from a finger when a user gradually increases contact pressure by pressing the pulse wave sensor 111 with the finger using a gradually increasing force. The first feature obtainer 320 may extract a peak-to-peak point of the pulse wave signal waveform by subtracting a negative (−) amplitude value in3 from a positive (+) amplitude value in2 of a waveform envelope in1 at each measurement time. Then, as illustrated in FIG. 4B, the first feature obtainer 320 may obtain the oscillometric envelope OW by plotting the peak-to-peak amplitude at each measurement time against the contact pressure value at the same point in time.

Upon obtaining the oscillometric envelope, the first feature obtainer 320 may extract a first feature from the obtained oscillometric envelope. Referring to FIG. 4B, the first feature obtainer 320 may obtain an amplitude value MA at a maximum peak point and/or a contact pressure value MP at the maximum peak point as the first feature from the oscillometric envelope OW. Further, the first feature obtainer 320 may further obtain contact pressure values SP and DP at predetermined left and right points that are distant from the contact pressure value MP at the maximum peak point, a combination of the extracted contact pressure values MP, SP, and DP, and the like, as the first feature. In this case, the contact pressure values SP and DP at the predetermined left and right points may be values that correspond to amplitude values having a preset peak ratio (e.g., 0.5 to 0.7) to the amplitude value MA at the maximum peak point, and the like. The preset ratio may be set to various values based on types of bio-information, user characteristics, and the like.

However, the first feature is not limited thereto, and by analyzing the waveform of the pulse wave signal, the first feature obtainer 320 may obtain information, such as time and amplitude values at points related to a propagation wave and a reflection wave, a time value and/or an amplitude value at a point where an amplitude of the pulse wave signal is maximum, an area of a section of the waveform of the pulse wave signal, a ratio between amplitude values at two or more points, and the like, as the first feature.

The second feature obtainer 330 may obtain a user's second feature. In this case, the second feature may include a variety of information related to the user.

For example, by referring to the storage 220 of FIG. 2, the second feature obtainer 330 may obtain individual information, such as a user's stature, weight, age, sex, health condition, reference bio-information (e.g., cuff blood pressure), and the like, as the second feature.

In another example, the second feature may include information on an environment, in which the pulse wave signal is measured, such as ambient humidity, ambient temperature, an object's temperature, and the like. The second feature obtainer 330 may obtain measurement environment information, such as ambient humidity, ambient temperature, an object's temperature, and the like during measurement of the pulse wave signal, by receiving the information input from a user, or by using a humidity/temperature measuring sensor mounted in an external device.

In yet another example, once the pulse wave signal is measured, the second feature obtainer 330 may obtain a DC component of the pulse wave signal, and may obtain an initial DC component value and/or a last DC component value, and the like as the second feature. In this case, the initial DC component value indicates a DC component value of the pulse wave signal at a time before a user applies force while touching the pulse wave sensor 111 with an object, and the last DC component value indicates a DC component value of the pulse wave signal at a time before contact is released after the user applies a predetermined force while touching the pulse wave sensor 111 with the object.

In still another example, the second feature obtainer 330 may obtain an initial contact area and/or a last contact area as the second feature. In this case, the initial contact area indicates a contact area at a time before a user applies force while touching the pulse wave sensor 111 with an object, and the last contact area indicates a contact area at a time before contact is released after the user applies a predetermined force while touching the pulse wave sensor 111 with the object.

However, the features are not limited to the above examples, and values obtained by combining the data described in the above examples or various other data, which are not described herein, may be obtained as the second feature.

Based on the obtained second feature of the user, the model selector 340 may select an estimation model for use in estimating bio-information from among a plurality of bio-information estimation models. In this case, the plurality of estimation models may be generated by classifying a plurality of training data into a plurality of groups based on the second feature and by customized training for each group.

For example, an estimation model of each group may be a model trained using deep learning including a Deep Neural Network (DNN). In this case, estimation models of at least some groups are not limited thereto, and may be generated by training using a DNN that is defined differently from other groups. For example, a first estimation model in a first group, having a second feature that is greater than or equal to a predetermined threshold, may be trained using a first DNN, and a second estimation model in a second group, having a second feature that is less than a predetermined threshold, may be trained using a second DNN that is different from the first DNN. In this case, the first DNN may be defined to have a first feature, extracted from training data of the first group, as input; and the second DNN may be defined to have a second feature, extracted from training data of the second group, as input.

Once the model selector 340 selects an estimation model, the estimator 350 may estimate bio-information based on the first feature obtained by the first feature obtainer 320 and/or the second feature obtained by the second feature obtainer 330.

For example, it is assumed that the second feature is defined as an initial contact area, and there is a first estimation model that is trained and generated using a first DNN for a first group having the initial contact area greater than or equal to 1.5, and there is a second estimation model that is trained and generated using a second DNN for a second group having the initial contact area less than 1.5. If an initial contact area obtained by the second feature obtainer 330 from a user is greater than or equal to 1.5, the model selector 340 may select the first estimation, model, and if an initial contact area obtained by the second feature obtainer 330 from a user is less than 1.5, the model selector 340 may select the second estimation model.

Further, once the model selector 340 selects the first estimation model, the estimator 350 may input the first feature into the first estimation model, and may obtain the output value as an estimated bio-information value; and by contrast, once the model selector 340 selects the second estimation model, the estimator 350 may input the first feature and the second feature into the second estimation model, and may obtain the output value as an estimated bio-information value.

Figure 5:
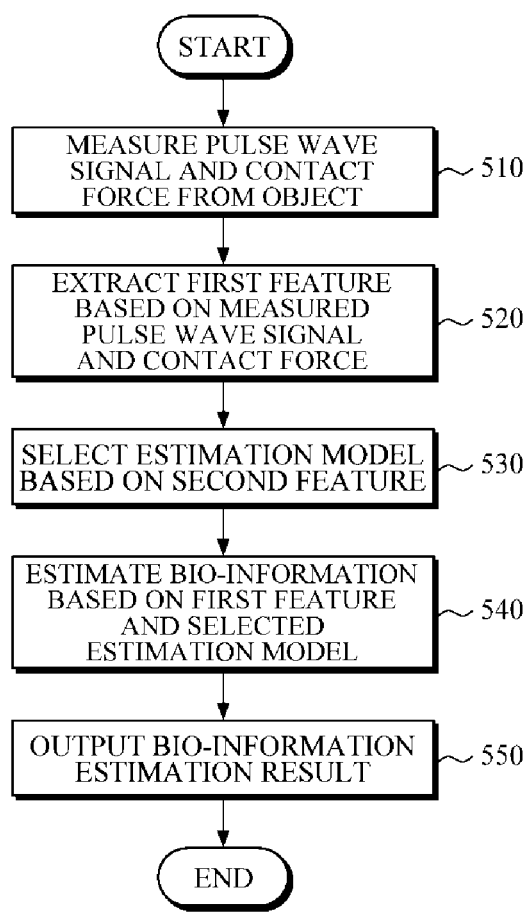
FIG. 5 is a flowchart illustrating a method of estimating bio-information, according to an example embodiment.

FIG. 5 is a flowchart illustrating a method of estimating bio-information, according to an example embodiment.

The method of estimating bio-information of FIG. 5 may be performed by the apparatuses 100 and 200 for estimating bio-information of FIGS. 1 and 2, which is described above in detail, and thus will be briefly described below.

Upon receiving a request for estimating bio-information, in operation 510, the apparatuses 100 and 200 for estimating bio-information may measure a pulse wave signal and a contact force from an object while a user touches a sensor part with the object and changes contact force. In this case, the request for estimating bio-information may be received from a user or an external device. Alternatively, for continuous estimation, it may be determined automatically at predetermined intervals that the request for estimating bio-information is received. Upon receiving the request for estimating bio-information, the apparatuses 100 and 200 for estimating bio-information may provide guide information on a contact position and a contact force so that the user may touch the sensor part with the object and may apply force thereto. In this case, the apparatuses 100 and 200 for estimating bio-information may guide the user to change the contact force by pressing the sensor part with a finger using a gradually increasing force, or by gradually decreasing the pressing force when the user touches the sensor part using a force greater than or equal to a predetermined threshold.

Then, in operation 520, the apparatuses 100 and 200 for estimating bio-information may extract a first feature based on the measured pulse wave signal and contact force. For example, by obtaining contact pressure based on the contact force and by obtaining an oscillometric envelope based on the pulse wave signal and the contact pressure, the apparatuses 100 and 200 for estimating bio-information may obtain a first feature from the oscillometric envelope. For example, the apparatuses 100 and 200 for estimating bio-information may obtain, as the first feature, a contact pressure value corresponding to a maximum amplitude value and contact pressure values at the right and left points that correspond to amplitude values having a preset peak ratio to the maximum amplitude value, and the like from the oscillometric envelope, but the first feature is not limited thereto.

Subsequently, in operation 530, the apparatuses 100 and 200 for estimating bio-information may select an estimation model for use in estimating bio-information based on a user's second feature. In this case, the estimation model may be trained and generated for each of a plurality of groups that are classified based on the second feature. The estimation model of each group may be trained using a DNN that is defined equally for the groups, or a DNN that is defined differently for at least some of the groups. For example, a first estimation model of a first group, having the second feature that is greater than or equal to a predetermined threshold, may be trained using a first DNN that has the first feature, extracted from a plurality of training data, as input, and a second estimation model of a second group, having the second feature that is less than a predetermined threshold, may be trained using a second DNN that has the first feature and the second feature, extracted from a plurality of training data, as input. In this case, the second feature may include an initial contact area, a last contact area, an initial DC component of the pulse wave signal, a last DC component of the pulse wave signal, and the like, but is not limited thereto.

Next, in operation 540, the apparatuses 100 and 200 for estimating bio-information may estimate bio-information based on the first feature extracted in operation 520 and the estimation model selected in operation 530. For example, upon selecting the first estimation model in operation 530 that is generated by training using the first DNN, the apparatuses 100 and 200 for estimating bio-information may input the first feature into the first estimation model, and upon selecting the second estimation model in operation 530 that is generated by training using the second DNN, the apparatuses 100 and 200 for estimating bio-information may input the first feature and the second feature into the second estimation model, and may obtain the output value as an estimated bio-information value.

Then, in operation 550, the apparatuses 100 and 200 for estimating bio-information may output a bio-information estimation result. The apparatuses 100 and 200 for estimating bio-information may output an estimated bio-information value, a variety of information used in estimating bio-information, health information monitored based on the estimated bio-information value, and the like by using various output devices such as a display, a speaker, a haptic device generating vibrations/tactile sensation, and the like.

Figure 6:
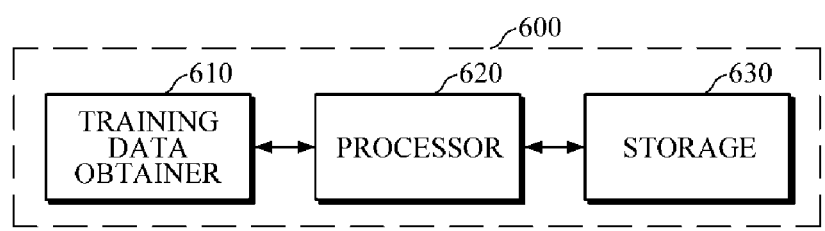
FIG. 6 is a block diagram illustrating an apparatus for estimating bio-information, according to an example embodiment.

FIG. 6 is a block diagram illustrating an apparatus 600 for estimating bio-information, according to an example embodiment.

Referring to FIG. 6, the apparatus 600 for estimating bio-information includes a training data obtainer 610, a processor 620, and a storage 630. The apparatus 600 for estimating bio-information may perform functions of the apparatuses 100 and 200 for estimating bio-information described above with reference to FIGS. 1 and 2. Accordingly, the following description will be given based on non-overlapping functions thereof.

The training data obtainer 610 may obtain training data for use in training a bio-information estimation model. The training data may include a plurality of pulse wave signals, a plurality of contact forces corresponding to each pulse wave signal, and a second feature.

In embodiments, the training data obtainer 610 may include the aforementioned sensor part 110 of FIGS. 1 and 2. The training data obtainer 610 may obtain the plurality of pulse wave signals and the plurality of contact forces from a user's object by using the pulse wave sensor and the force sensor of the sensor part 110. For example, the training data obtainer 610 may obtain a plurality of pulse wave signals and a plurality of contact forces as training data from an user, or may obtain a pulse wave signal and a contact force from each of a plurality of users. Further, while obtaining the pulse wave signal, the training data obtainer 610 may obtain a second feature such as an initial contact area of an object and the like. In addition, the training data obtainer 610 may build up data by using the obtained pulse wave signal.

In embodiments, the training data obtainer 610 may include the communication interface 230 of FIG. 2. For example, the training data obtainer 610 may communicate with an apparatus for estimating bio-information, which is used by each user, through the communication interface 230, and may receive the pulse wave signal, the contact force, and the second feature of each user as training data from each apparatus for estimating bio-information.

The processor 620 may extract each first feature based on each pulse wave signal and contact force of the obtained training data. Further, the processor 620 may classify the training data into a plurality of groups based on the second feature corresponding to each pulse wave signal, and may generate an estimation model for each group by training the estimation model using a DNN, which is defined for each group based on the first feature and/or the second feature.

For example, if the second feature is greater than or equal to a predetermined threshold, the processor 620 may classify the second feature as a first group, and if the second feature is less than a predetermined threshold, the processor 620 may classify the second feature as a second group. For example, in the case in which the second feature is an initial contact area, if the initial contact area is greater than or equal to 1.5, the processor 620 may classify the second feature as the first group, and if the initial contact area is less than 1.5, the processor 620 may classify the second feature as the second group. However, the processor 620 is not limited thereto, and may classify data into three or more groups by setting a plurality of threshold values.

Further, by training using a DNN that is pre-defined for each group, the processor 620 may generate, for example, a first estimation model for the first group and a second estimation model for the second group. In this case, the first estimation model may be trained using a first DNN having the first feature as input and the second estimation model may be trained using a second DNN having the first feature and the second feature as input.

Upon generating or updating the bio-information estimation model, the processor 620 may transmit the estimation model to other apparatus for estimating bio-information that has requested the estimation model, so that the apparatus may update the estimation model. Alternatively, the processor 620 may periodically transmit the estimation model to other apparatuses for estimating bio-information, so that the apparatuses may update the estimation model.

The storage 630 may store the training data obtained by the training data obtainer 610, and the estimation model generated by the processor 620. Upon receiving a request for estimating bio-information, the processor 620 may estimate bio-information by referring to the bio-information estimation model stored in the storage 630, FIG. 7 is a diagram illustrating a wearable device 700 according to an example embodiment, to which the aforementioned embodiments of the apparatuses 100, 200, and 600 for estimating bio-information are applied.

Figure 7:
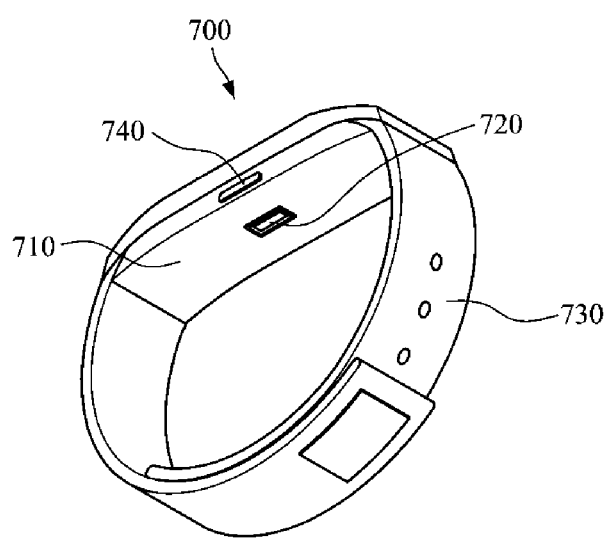
FIG. 7 is a diagram illustrating a wearable device according to an example embodiment.

Referring to FIG. 7, the wearable device 700 includes a main body 710 and a strap 730.

The strap 730 may be flexible, and may be connected to both ends of the main body 710 to be bent around a user's wrist or may be bent in a manner that allows the strap 730 to be detached from a user's wrist. Alternatively, the strap 730 may be formed as a band that is not detachable. In this case, air may be injected into the strap 730 or an airbag ma be included in the strap 730, so that the strap 730 may have elasticity according to a change in pressure applied to the wrist, and the change in pressure of the wrist may be transmitted to the main body 710.

A battery, which supplies power to the wearable device 700, may be embedded in the main body 710 or the strap 730.

Further, a sensor part 720 is mounted on one side of the main body 710. The sensor part 720 may include a pulse wave sensor that measures a pulse wave signal from blood vessel tissue of the wrist that is in contact with the pulse wave sensor; and a force sensor that measures a contact force between the wrist and the pulse wave sensor. The pulse wave sensor may include one or more light sources for emitting light onto the wrists, and a detector for detecting light reflected or scattered from the skin of the wrist and the blood vessel tissue. In this case, each of the light sources may emit light of different wavelengths, and may be disposed at different distances from the detector.

When a user changes contact pressure between the wrist and the sensor part 720, the sensor part 720 may measure a pulse wave signal and a contact force. For example, the user may change contact pressure between the wrist and the sensor part 720 by pressing a display, mounted on one surface of the main body 710, e.g., a surface opposite to the sensor part 720, with a finger of the other hand with a gradually increasing force while wearing the main body 710. Alternatively, the user may change a thickness of the wrist by making hand movements, e.g., slowly opening the hand after clenching the first while wearing the main body 710 on the wrist. In this case, the change in the thickness of the wrist leads to a change in tension of the strap wrapped around the wrist, thereby causing a change in contact pressure between the wrist and the sensor part 720.

In addition, the main body 710 may include a processor, which may estimate bio-information by using the pulse wave signal, the contact force, and the like, and may control various other functions of the wearable device 700.

In response to a user's request for estimating bio-information, the processor may generate a control signal to control the sensor part 720. The processor may obtain an oscillometric envelope based on the pulse wave signal and the contact force, and may obtain a first feature by using the obtained oscillometric envelope. Further, the processor may obtain a second feature related to a user. Based on the second feature, the processor may select one estimation model for use in estimating bio information from among a plurality of bio-information estimation models, and may estimate bio-information by using the selected estimation model and the first feature. As described above, the estimation model may be pre-generated using the wearable device 700 or an external apparatus for estimating bio-information, or may be generated by classifying a plurality of training data into a plurality of groups based on the second feature, and by training using a DNN that is pre-defined for each group.

Upon receiving the request for estimating bio-information from a user, the processor may provide guide information on contact pressure for the user through a display, so that the user may change contact pressure between the sensor part 720 and the object by applying pressure to the main body 710.

In this case, the display may be mounted on a front surface of the main body 710, and may visually output guide information on contact pressure and/or a bio-information estimation result.

A storage may be mounted in the main body 710, and may store a variety of information processed by the processor, and a variety of reference information for estimating bio-information.

Further, the wearable device 700 may include a manipulator 741 that receives a control instruction of a user and transmits the received control instruction to the processor. The manipulator 740 may be mounted on a side surface of the main body 710, and may include a function for inputting an instruction for power on/off of the wearable device 700.

Moreover, the wearable device 700 may include a communication interface for transmitting and receiving various data to and from an external device, and various other modules for performing additional functions provided by the wearable device 700.

Figure 8:
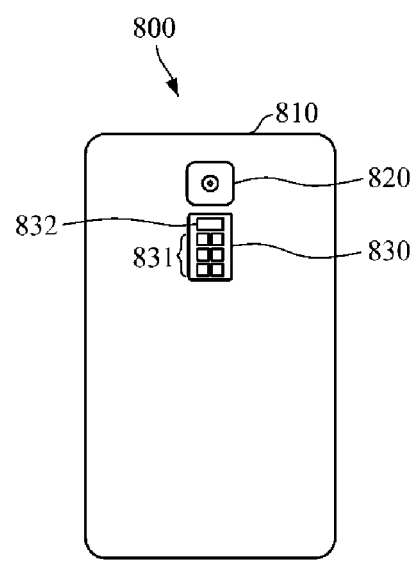
FIG. 8 is a diagram illustrating a smart device according to an example embodiment.

FIG. 8 is a diagram illustrating a smart device 800 according to an example embodiment, to which the embodiments of the apparatus for estimating bio-information are applied. In this case, the smart device may be a smartphone, a tablet PC, and the like.

Referring to FIG. 8, the smart device 800 includes a main body 810 and a sensor part 830 mounted on one surface of the main body 810. The sensor part 830 may include a pulse wave sensor, including one or more light sources 831 and a detector 832, and a force sensor. As illustrated in FIG. 8, the sensor part 830 may be mounted on a rear surface of the main body 810, but is not limited thereto.

In addition a display may be mounted on a front surface of the main body 810. The display may visually display a bio-information estimation result and the like. The display may include a touch screen, and may receive a variety of information input through the touch screen and transmit the information to the processor.

Moreover, an image sensor 820 may be mounted in the main body 810. When a user's finger approaches the sensor part 830 to measure a pulse wave signal, the image sensor 820 may capture an image of the finger and may transmit the captured image to the processor. In this case, based on the image of the finger, the processor may identify a relative position of the finger with respect to an actual position of the sensor part 830, and may provide the relative position of the finger to the user through the display, so that pulse wave signals may be measured with improved accuracy.

By extracting a first feature based on the pulse wave signal and the contact force, and by selecting an estimation model for use in estimating bio-information based on a second feature of a user, the processor may estimate bio-information by using the first feature and the selected estimation model, which is described above such that a detailed description thereof, will be omitted.

The embodiments can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments for realizing the embodiments can be readily deduced by programmers in the technical field to which the embodiments pertain.

The inventive concepts have been described herein with regard to example embodiments. However, it will be understood by those skilled in the art that various changes and modifications can be made without changing technical conception and features of the example embodiments. Thus, it is clear that the above-described example embodiments are illustrative in all aspects and are not intended to limit the inventive concepts.

What is claimed is:

1. An apparatus for estimating bio-information of a subject, the apparatus comprising:
a sensor part configured to measure a pulse wave signal of a body surface of the subject and configured to measure a contact force of the body surface, while the body surface is in contact with the sensor part,
wherein the sensor part comprises:
a pulse wave sensor comprising:
a light source configured to emit light onto the body surface; and
a detector configured to detect light that is reflected or scattered from the body surface; and
a force sensor configured to measure the contact force when the body surface comes into contact with the pulse wave sensor and the body surface applies pressure to the pulse wave sensor, and
a contact area sensor,
wherein the contact area sensor is configured to measure a contact area of the sensor part with which the body surface is in contact, while the body surface is in contact with the sensor part and the body surface applies pressure to the sensor part; and
a processor configured to:
extract a first feature from the measured pulse wave signal and the measured contact force;
select an estimation model from a plurality of estimation models, based on a second feature of the subject; and
estimate the bio-information, by inputting the extracted first feature in the selected estimation model, wherein the bio-information is a physiological feature of the subject,
wherein the estimation of the bio-information is performed upon the subject activating a request for bio-information in a wearable device,
wherein a first estimation model of a first group corresponding to the second feature when the second feature is greater than or equal to a predetermined threshold, is obtained by training a first deep neural network (DNN), using the first group, the first estimation model being one of the plurality of estimation models and
a second estimation model of a second group corresponding to the second feature when the second feature is less than the predetermined threshold, is obtained by training a second DNN different from the first DNN, using the second group, the second estimation model being one of the plurality of estimation models,
wherein the processor is configured to extract the first feature further based on the measured contact area.

2. The apparatus of claim 1, wherein the plurality of estimation models are obtained by classifying a plurality of training data into groups, based on the second feature, and by training a plurality of deep neural networks (DNNs), respectively using the groups into which the plurality of training data is classified, the plurality of DNNs including the first DNN and the second DNN, and the groups include the first group and the second group.

3. The apparatus of claim 1, wherein a first input of the first DNN comprises the first feature, and
a second input of the second DNN comprises the first feature and the second feature.

4. The apparatus of claim 1, wherein the second feature comprises any one or any combination of an initial contact area of the sensor part with which the body surface is in contact, a last contact area of the sensor part with which the body surface is in contact, an initial direct current (DC) component value of the measured pulse wave signal, a last DC component value of the measured pulse wave signal, reference bio-information, a stature of the subject, a weight of the subject, an age of the subject, a sex of the subject, ambient humidity, and ambient temperature.

5. The apparatus of claim 1, wherein the processor is further configured to:

obtain a contact pressure, based on the measured contact force and the measured contact area;
obtain an oscillometric envelope representing an amplitude of the measured pulse wave signal versus the obtained contact pressure; and
extract the first feature from the obtained oscillometric envelope.

6. The apparatus of claim 1, wherein the bio-information comprises any one or any combination of a blood pressure, a vascular age, an arterial stiffness, an aortic pressure waveform, a vascular compliance, a stress index, and a degree of fatigue of the subject.

7. The apparatus of claim 1, wherein the processor is further configured to display instructions for placement of the sensor part and the body part based on the measured contact area and measured contact force to provide an improved bio-information estimate.

* * * * *